United States Patent
Hart

(10) Patent No.: US 10,010,444 B2
(45) Date of Patent: Jul. 3, 2018

(54) BREATHING ASSIST DEVICE

(75) Inventor: Christopher Patrick Hart, Queensland (AU)

(73) Assignee: Oventus Medical Limited, Brisbane, Queensland (AU)

(*) Notice: Subject to any disclaimer, the term of this patent is extended or adjusted under 35 U.S.C. 154(b) by 16 days.

(21) Appl. No.: 14/118,416

(22) PCT Filed: May 18, 2012

(86) PCT No.: PCT/AU2012/000565
§ 371 (c)(1),
(2), (4) Date: Jan. 24, 2014

(87) PCT Pub. No.: WO2012/155214
PCT Pub. Date: Nov. 22, 2012

(65) Prior Publication Data
US 2014/0130807 A1    May 15, 2014

(30) Foreign Application Priority Data

May 19, 2011    (AU) .................................. 2011901952

(51) Int. Cl.
*A61F 5/56* (2006.01)
(52) U.S. Cl.
CPC ..................... *A61F 5/566* (2013.01)
(58) Field of Classification Search
USPC .............. 128/848, 859, 861, 200.26, 207.14
See application file for complete search history.

(56) References Cited

U.S. PATENT DOCUMENTS

| 2,820,457 | A | * | 1/1958 | Phillips ............. A61M 16/0488 |
| | | | | 128/200.26 |
| 4,169,473 | A | | 10/1979 | Samelson |
| 4,170,230 | A | * | 10/1979 | Nelson ............. A61M 16/0488 |
| | | | | 128/848 |
| 4,304,227 | A | | 12/1981 | Samelson |
| 4,676,240 | A | | 6/1987 | Gardy |

(Continued)

FOREIGN PATENT DOCUMENTS

| JP | 2010-09615 A | 2/2010 |
| JP | 2010-142497 A | 7/2010 |

(Continued)

OTHER PUBLICATIONS

JP2010142497_translation.PDF: machine translation of Japanese patent application No. 2010142497A.*

(Continued)

*Primary Examiner* — Ophelia A Hawthorne
*Assistant Examiner* — Caitlin Carreiro
(74) *Attorney, Agent, or Firm* — Panitch Schwarze Belisario & Nadel LLP

(57) ABSTRACT

Apparatus for providing breathing assistance, the apparatus including a body including a recess for receiving teeth of a user to thereby position the body within an oral cavity of the user, a first opening extending beyond lips of a user to allow air from outside the oral cavity to be drawn in through the opening, a second opening provided in the oral cavity to allow air to be directed into a posterior region of the oral cavity and a channel connecting the first and second openings, the channel extending through at least part of a buccal sulcus of the user.

16 Claims, 12 Drawing Sheets

(56) References Cited

U.S. PATENT DOCUMENTS

| | | | |
|---|---|---|---|
| 5,092,346 | A | 3/1992 | Hays et al. |
| 5,465,734 | A | 11/1995 | Alvarez et al. |
| 5,537,994 | A | 7/1996 | Thornton |
| 5,792,067 | A * | 8/1998 | Karell ............... A61N 1/0548 |
| | | | 128/848 |
| 5,954,048 | A | 9/1999 | Thornton |
| 5,983,892 | A | 11/1999 | Thornton |
| 6,055,989 | A * | 5/2000 | Rehnke ............ A61B 17/0218 |
| | | | 128/898 |
| 6,374,824 | B1 | 4/2002 | Thornton |
| 6,474,339 | B1 | 11/2002 | Grosbois et al. |
| 8,931,487 | B2 | 1/2015 | Razmovski |
| 2002/0139375 | A1 | 10/2002 | Kulick |
| 2004/0194787 | A1 | 10/2004 | Miller |
| 2005/0081859 | A1 | 4/2005 | Scarberry et al. |
| 2005/0103331 | A1 | 5/2005 | Wedemeyer |
| 2005/0150504 | A1 | 7/2005 | Heeke et al. |
| 2006/0169289 | A1 | 8/2006 | Zacco |
| 2006/0174897 | A1 | 8/2006 | Sarkisian |
| 2006/0219250 | A1 * | 10/2006 | Farrell ............... A63B 71/085 |
| | | | 128/859 |
| 2007/0235037 | A1 | 10/2007 | Thornton |
| 2008/0216843 | A1 * | 9/2008 | Jiang ................. A61F 5/566 |
| | | | 128/848 |
| 2008/0233531 | A1 | 9/2008 | Raby et al. |
| 2008/0257358 | A1 | 10/2008 | Stern et al. |
| 2009/0120446 | A1 | 5/2009 | Vaska et al. |
| 2009/0241969 | A1 | 10/2009 | Walker |
| 2010/0132720 | A1 | 6/2010 | Razmovski |
| 2010/0311003 | A1 * | 12/2010 | Kozlov ............... A61F 5/566 |
| | | | 433/2 |
| 2011/0220124 | A1 * | 9/2011 | Vaska ................. A61F 5/566 |
| | | | 128/848 |
| 2011/0232652 | A1 | 9/2011 | Levendowski et al. |
| 2012/0143003 | A1 * | 6/2012 | Anca ................. A61M 16/0488 |
| | | | 600/114 |
| 2012/0145166 | A1 | 6/2012 | Fallon et al. |
| 2013/0074851 | A1 | 3/2013 | Herman et al. |
| 2013/0081640 | A1 | 4/2013 | Herman et al. |
| 2015/0101615 | A1 | 4/2015 | Podmore et al. |
| 2015/0272773 | A1 | 10/2015 | Rico et al. |

FOREIGN PATENT DOCUMENTS

| | | |
|---|---|---|
| JP | 2010142497 A * | 7/2010 |
| WO | 2010038171 A1 | 4/2010 |
| WO | 2010141868 A2 | 12/2010 |
| WO | 2012140021 A2 | 10/2012 |
| WO | 2012155214 A1 | 11/2012 |
| WO | 2013086586 A1 | 6/2013 |
| WO | 2013134235 A1 | 9/2013 |
| WO | 2014110432 A2 | 7/2014 |
| WO | 2014133969 A1 | 9/2014 |
| WO | 2014144717 A2 | 9/2014 |

OTHER PUBLICATIONS

Int'l Search Report dated Jun. 13, 2012 in Int'l Application No. PCT/AU2012/000565.

Office Action dated May 27, 2016 in EP Application No. 12785448.7.

Office Action dated Dec. 15, 2015 in AU Application No. 2012255625.

Extended Search Report dated Oct. 27, 2014 in EP Application No. 12785448.7.

Examination Report dated Jan. 18, 2016 in AU Application No. 2012255625.

Int'l Search Report and Written Opinion dated Oct. 14, 2016 in Int'l Application No. PCT/AU2016/050696.

Int'l Preliminary Report on Patenability dated Oct. 4, 2016 in Int'l Application No. PCT/AU2015/050144.

Int'l Search Report and Written Opinion dated Jun. 29, 2016 in Int'l Application No. PCT/AU2015/050144.

Examination Report dated May 19, 2017 in AU Application No. 2015240431.

Extended Search Report dated Jul. 31, 2017 in EP Application No. 15773894.9.

Int'l Search Report and Written Opinion dated Jun. 13, 2017 in Int'l Application No. PCT/AU2017/050271.

Roberts et al., "Proper Depth of Placement of Oral Endotracheal Tubes in Adults Prior to Radiographic Confirmation," Academic Emergency Medicine, vol. 2, No. 2, pp. 20-24 (Jan. 1995).

* cited by examiner

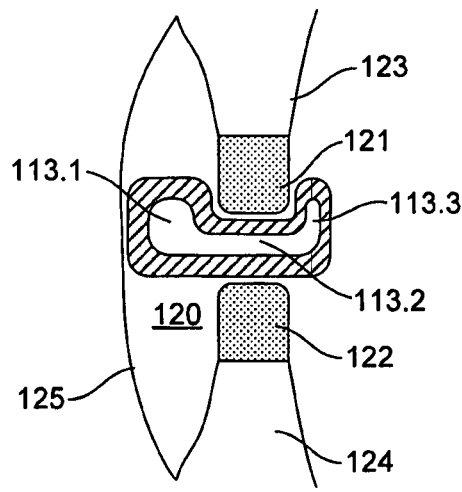 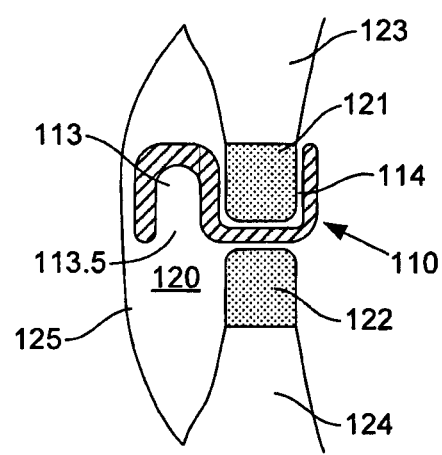
Fig. 2A  Fig. 2B
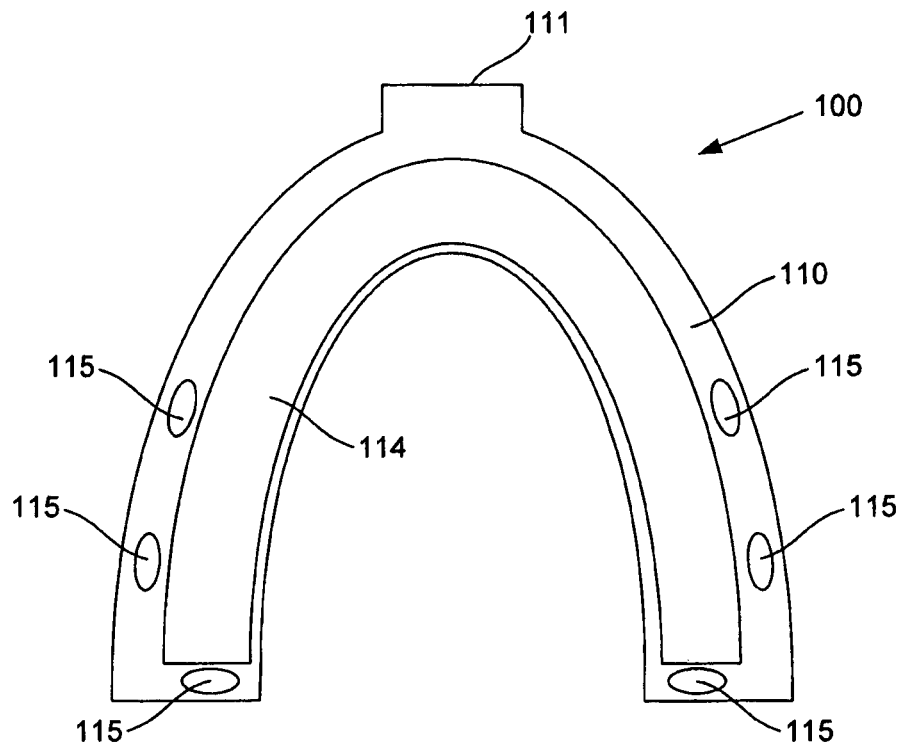
Fig. 2C

BREATHING ASSIST DEVICE

CROSS-REFERENCE TO RELATED APPLICATION

This application is a Section 371 of International Application No. PCT/AU2012/000565, filed May 18, 2012, which was published in the English language on Nov. 22, 2012 under International Publication No. WO 2012/155214 A1, and the disclosure of which is incorporated herein by reference.

BACKGROUND OF THE INVENTION

The present invention relates to apparatus for providing breathing assistance, and in particular an apparatus for providing breathing assistance during sleeping.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Snoring arises due to vibration of soft tissues within the respiratory pathways of an individual, and is typically caused by obstructed air movement during breathing while sleeping. Snoring can arise from a range of different physical causes such as blocked sinuses, and typically occurs when the muscles of the upper throat relax during sleep.

Snoring can also be associated with Obstructive Sleep Apnoea (OSA), which is caused by obstruction of the upper airway and results in repetitive pauses in breathing during normal sleep. Individuals having OSA often suffer from daytime sleepiness and fatigue associated with significant levels of sleep disturbance, whilst a partners sleep patterns are also often disturbed by associated snoring.

Current therapy for treatment of OSA can include lifestyle changes, the use of mechanical devices, such as oral or nasal devices that augment the airway, surgical procedures to enlarge and stabilize the airway during sleep, and continuous or variable positive airway pressure (CPAP, VPAP) devices.

However, surgical procedures can be severe and are not therefore widely used unless absolutely necessary. Whilst CPAP and VPAP devices have had a positive impact, these can be uncomfortable to wear for prolonged time periods, are expensive, and are often noisy, which can in turn lead to additional sleep disturbance. As a result, surgery, VPAP and CPAP treatment have limited application in treating sleep apnoea, and are not generally considered appropriate treatment for snoring.

In terms of other mechanical devices, nasal devices have been used that dilate the nasal airway using traction or splinting. However, these have typically not had much success and can be uncomfortable for a user.

US2004/194787 describes an anti-snoring device that includes a flexible hollow tube for insertion into the user's mouth, having proximal and distal ends and an outer perimeter. The tube includes an extraoral segment at its proximal end, an intraoral segment at its distal end and an intermediate segment extending therebetween. The extraoral and intraoral segments each include at least one opening. The extraoral segment is for extending beyond the user's outer lips, the intermediate segment is of a sufficient length for extending along the buccopharyngeal pathway of the user's mouth, and the intraoral segment is of a sufficient length for extending beyond a retromolar space in the user's mouth, into the oropharynx and terminating between the posterior tongue and the soft palate. The anti-snoring device also includes a stop extending from the outer perimeter of the tube on the intraoral segment for securing the intraoral segment within the user's oropharynx. However, whilst this arrangement can assist in providing an additional airway, and hence reduce snoring and apnoea events, it can be uncomfortable to wear and can move within the mouth during use, which can reduce device effectiveness and in turn lead to additional breathing problems.

US2005/150504 describes a device which is removably insertable in the mouth for facilitating breathing while sleeping which provides a clear unobstructed airway by protrusive positioning of the mandible and/or delivery of pressurized air to the back of the mouth. The device has upper and lower tooth-contacting members and an airway defined between them, and is designed specifically for use with CPAP machines. Consequently, this device can only be used in limited circumstances, where CPAP machines are available, and is only used in the treatment of sleep apnoea.

SUMMARY OF THE PRESENT INVENTION

In a broad form the present invention seeks to provide apparatus for providing breathing assistance, the apparatus including:
  a) a body for positioning within an oral cavity of the user;
  b) a first opening extending beyond lips of a user to allow air from outside the oral cavity to be drawn in through the opening;
  c) a second opening provided in the oral cavity to allow air to be directed into a posterior region of the oral cavity; and,
  d) a channel connecting the first and second openings, the channel extending through at least part of a buccal sulcus of the user.

Typically the body includes a recess for receiving teeth of the user.

Typically the recess is for receiving the user's maxillary teeth.

Typically at least part of the channel extends between the user's buccal mucosa and teeth.

Typically at least part of the channel extends between the user's maxillary and mandibular teeth.

Typically the channel includes a channel opening extending along at least part of the channel.

Typically the channel opening faces a user's mandible.

Typically the channel is substantially U-shaped.

Typically the apparatus includes at least two second openings.

Typically the channel directs air through a hammular notch of the user.

Typically the channel extends behind teeth of the user.

Typically the second opening being provided on a lingual side of the teeth.

Typically the channel directs air into a region between the hard and soft palettes of the user.

Typically at least the recess is moulded for the user.

Typically at least the body includes a lingual flange for engaging mandibular teeth to thereby maintain mandibular position.

Typically the lingual flange is mounted on an second side of the body, the recess being provided on an opposing first side of the body.

Typically the lingual flange is movably mounted to the body to thereby allow adjustment of a user's mandibular position.

Typically the lingual flange defines a recess for receiving a user's tongue.

Typically the body includes a tongue recess for receiving a user's tongue.

Typically the tongue recess is provided in a second side of the body, the recess being provided on an opposing first side of the body.

Typically the recess engages teeth of an upper jaw of the user, thereby retaining the body in position when a user opens their mouth.

Typically the body is made of heat-cured acrylic resin.

BRIEF DESCRIPTION OF THE DRAWINGS

An example of the present invention will now be described with reference to the accompanying drawings, in which:

FIG. 2A is schematic cross-sectional view along the line A-A' of a first example of an alternative channel arrangement for the apparatus of FIG. 1A;

FIG. 2B is a schematic cross-sectional view along the line A-A' of a second example of an alternative channel arrangement for the apparatus FIG. 1A;

FIG. 2C is a schematic underside view of a third example of an alternative channel arrangement for the apparatus FIG. 1A;

DETAILED DESCRIPTION OF THE PREFERRED EMBODIMENTS

Figure 1A:
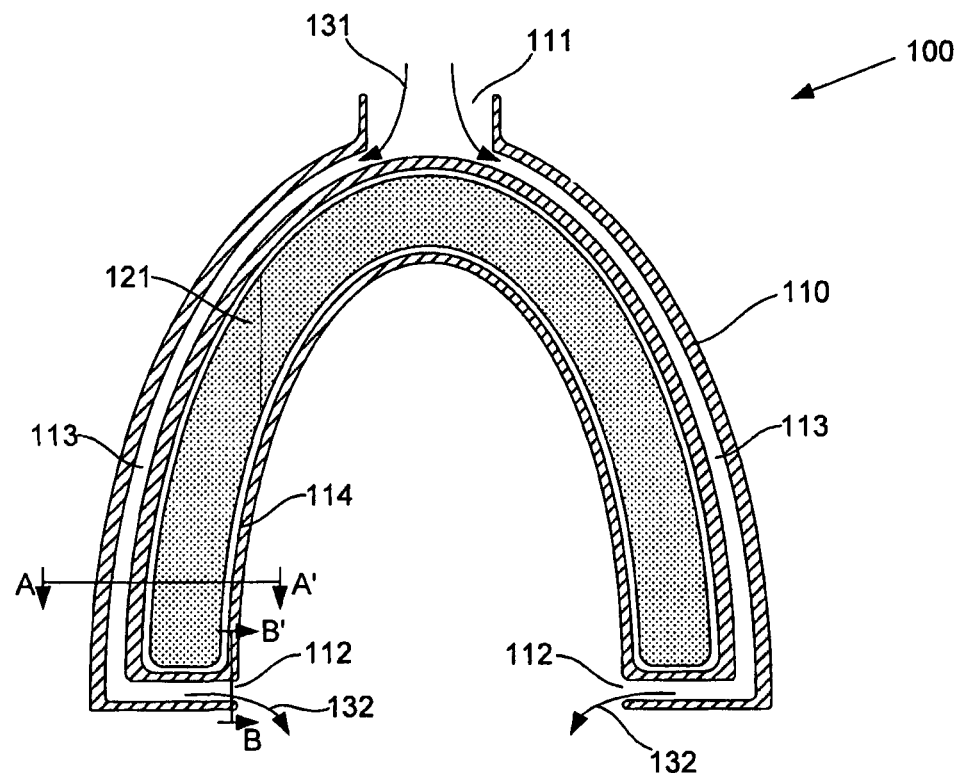
FIG. 1A is a schematic cross-sectional view of apparatus for providing breathing assistance.

An example of a breathing assist apparatus will now be described with reference to FIGS. 1A to 1E.

In this example, the apparatus 100 includes a body 110 having a first opening 111 and two second openings 112 connected to the first opening via respective channels 113. Although two second openings 112 and channels 113 are shown, this is for the purpose of example only, and as an alternative, a single channel 113 and second opening 112 may be used. The body 110 also includes a recess 114 for receiving teeth of the user, to thereby position the body 110 within the oral cavity of the user. In one particular example, the recess 114 defines a bite for receiving the maxillary teeth of the user, although this is not essential and other arrangements can be used.

In use, the body 110 is positioned so that the first opening 111 extends between the users lips, with the channels 113 extending along at least part of a buccal sulcus 120 of the user. In this regard, the buccal sulcus is a region between the maxillary and mandibular teeth 121, 122 and associated gingiva 123, 124 and the cheeks 125 of the user.

As a result of this arrangement, during respiration, air can enter the apparatus 100 via the first opening 111, as shown by the arrows 131, pass along the channel 113, via the buccal sulcus, to the second openings 112. The second openings 112 are typically provided towards a posterior of the user's oral cavity, on a lingual side of the user's teeth, so that air is directed into the posterior of the oral cavity, as shown by the arrows 132. In one particular example, the channels 113 and second openings 112 are provided so that air flows through the region of the user's hamular notch so that air flow enters the oral cavity in the vicinity of a junction between the hard and soft pallets.

Providing air flow directly into a posterior portion of the user's oral cavity has a number of benefits. In particular, this avoids obstructions created by the nasal cavity, soft palate and tongue which can lead to snoring and apnoea events, and helps reduce the drying effects of air flow, which can in turn lead to user discomfort. This makes the apparatus comfortable to wear whilst ensuring an unobstructed air flow thereby preventing snoring and apnoea events.

Thus, for example, nasal obstructions can be bypassed by air flow running along the airway between the user's lips, into the buccal sulcus and through an area over or behind the wisdom teeth and the hamular notch. The airway feeds air onto the junction of the hard and soft palate, thereby bypassing the nasal airway or adding to it in the case of a partial obstruction. Furthermore, air flowing below or on both sides of the soft palette helps prevent collapse of the soft palate, which can in turn lead to additional obstruction.

It will be appreciated by a person skilled in the art that a number of variations are possible, as will now be described in further detail.

For example, a range of different configurations of channel 113 can be used. In the above described example, the channel 113 is contained solely within the buccal sulcus 120. However this is not essential and as an alternative the channel 113 can be extended in a lateral direction so that at least part of the channel 113 passes between the maxillary and mandibular teeth 121, 122 as shown in FIG. 2A.

In this example, the channel 113 includes a first portion 113.1 extending through the buccal sulcus 120, a second portion 113.2 extending between the maxillary and mandibular teeth 121, 122, and a third portion 113.3 extending along a lingual side of the teeth. It will be appreciated that this allows the channel 113 to have an increased cross sectional area, which in turn allows for increased air flow along the channel 113, thereby maximising the breathing assistance provided.

Figures 1B, 1C:
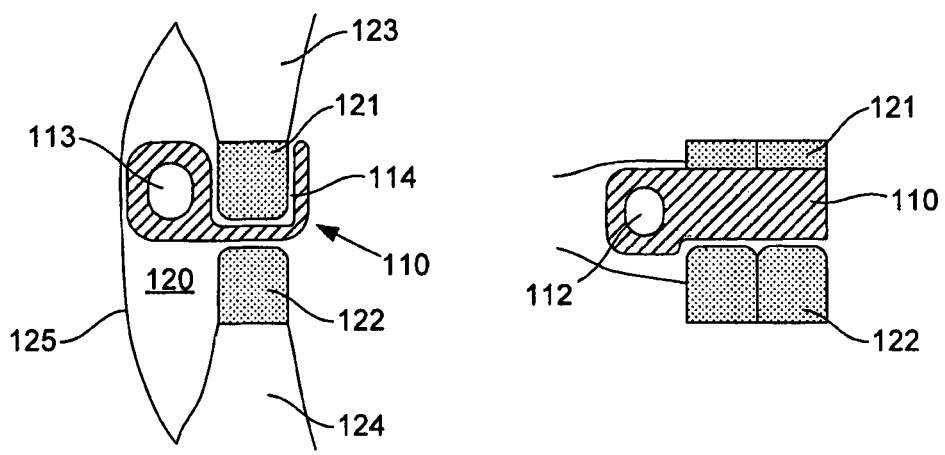
FIG. 1B is a cross-sectional view along the line A-A' on FIG. 1A.
FIG. 1C is a schematic cross-sectional view along the line B-B' of FIG. 1A.
Figure 1D:
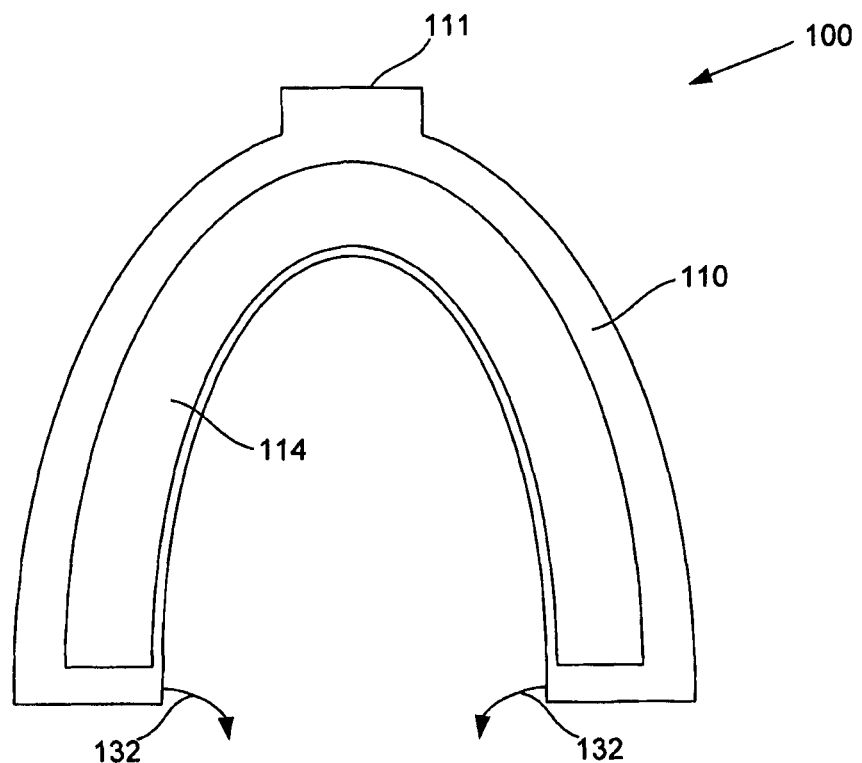
FIG. 1D is schematic plan view of the apparatus of FIG. 1A.
Figure 1E:
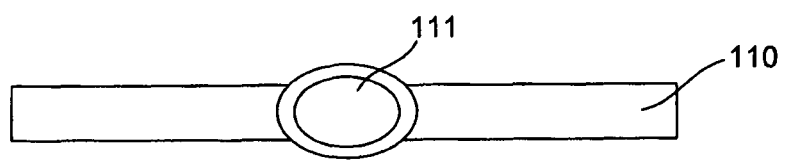
FIG. 1E is a schematic front view of the apparatus of FIG. 1A.

Whilst the channel 113 is shown as completely enclosed in the examples of FIGS. 1B and 2A this is not essential, and the channel could be formed from an open channel, an example of which is shown in FIG. 2B.

In this example, the channel includes a channel opening 113.5, extending along an underside of the apparatus 100, so that the channel opening 113.5 faces towards the user's lower jaw, or mandibles. This can assist with drainage of fluids, such as saliva, from the channel 113, thereby helping maintain an open pathway for air flow.

However, one disadvantage of the use of an open channel is that air can exit the channel 113 along the entire length of the channel 113. This can reduce the effectiveness of the apparatus and lead to drying of the user's soft palette.

Accordingly an alternative arrangement can be used, in which the channel 113 includes a number of channel openings 115 along the channel length, as shown for example in FIG. 2C.

The channel openings 115, which may be provided at any suitable location along the channel length, can be provided in an upper face of the channel 113 so that they are facing the maxilla, thereby allowing air to exit the channel. This can assist in providing adequate airflow into the posterior of the user's oral cavity, as required. Alternatively and/or additionally, the channel openings 115 can be provided in a lower face of the channel 113, so that they face the mandibles, thereby allowing saliva to drain from the channel 113.

Figure 3A:
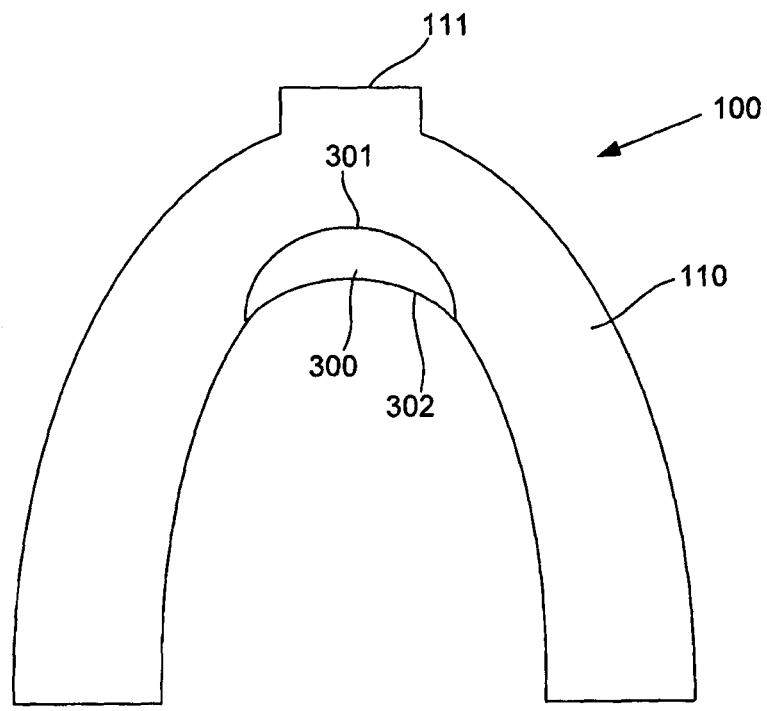
FIG. 3A is a schematic underside view of a third example of a breathing assist apparatus.
Figure 3B:
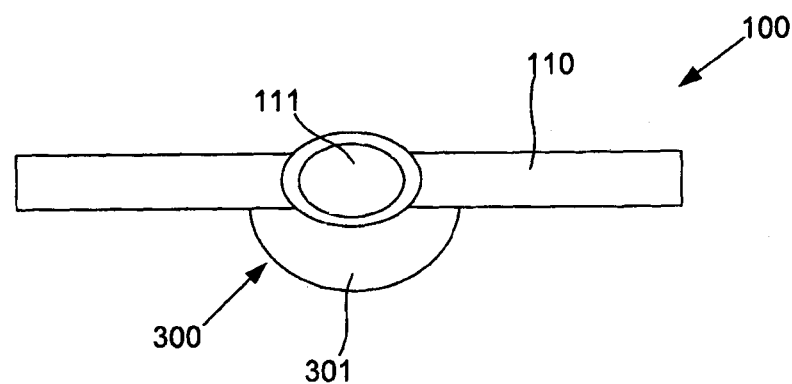
FIG. 3B is a schematic front view of the apparatus FIG. 3A.
Figure 3C:
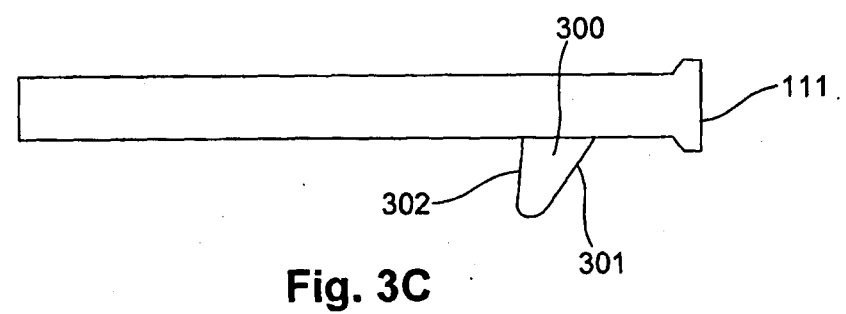
FIG. 3C is a schematic side view of the apparatus FIG. 3A.

In addition to providing an airway, the apparatus 100 can also be adapted to assist in providing alignment between the upper and lower jaws. An example of an arrangement suitable for this is shown in FIGS. 3A to 3C.

In this example, the apparatus includes a lingual flange 300, which extends from the body 110 as shown. The lingual flange 300 is provided on a second side of the body 110 (corresponding to an underside in use), opposing a first side of the body (corresponding to an upperside in use) that contains the recess 114, so that the lingual flange extends towards the user's lower jaw. The lingual flange 300 includes a first face 301, which in use, engages a lingual side of the user's mandibular incisors. By providing the lingual flange 300 at an appropriate position on the body 110, this can be used to control the relative positions of the maxillary and mandibular jaws.

In this regard, it is known that temporomandibular joint disorder (TMD) arises when the upper and lower jaws are misaligned. This may be naturally occurring or can result from injury, or the like. Regardless, such jaw misalignment tends to contribute to airway obstructions by changing the shape of the upper airway, and moving the tongue towards the posterior of the oral cavity, which can in turn exacerbate issues associated with OSA and snoring. Accordingly, providing the lingual flange 300 at an appropriate location allows the jaws of the user to be aligned thereby reducing the effects of TMD, and hence further reducing the likelihood of snoring and OSA.

In addition, a second side 302 of the lingual flange can be provided to define a pocket for receiving the user's tongue. In this regard, the second side 302 is of a concave shape, so that when the tongue abuts against the lingual flange 300 a suction effect is created, thereby helping to retain the user's tongue towards the anterior of the oral cavity, which in turn helps further reduce airway obstruction caused by the position of the user's tongue.

A specific apparatus is shown in FIGS. 4A to 4J, in which an example device is arranged with respect to moulds of upper and lower jaws 401, 402. Similar features are identified by similar reference numerals and these will not therefore be described in further detail.

As shown in FIG. 4C to 4K, air enters the first opening 111 (arrows 131), passes along the channels 113 (arrows 133) and exits the channel 113 via the second openings 112 (arrows 132). Thus, it will be appreciated that this provides airflow via the buccal sulcus 120, as well as between the user's teeth, to the posterior of the user's oral cavity, as described above.

Figure 4A:
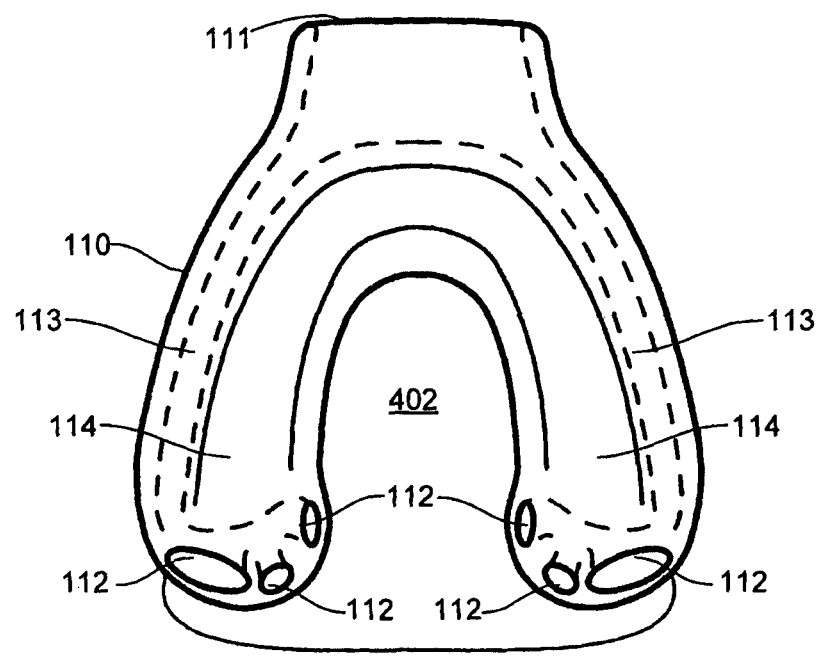
FIG. 4A is a schematic plan view of a specific example of a breathing assist apparatus.
Figure 4B:
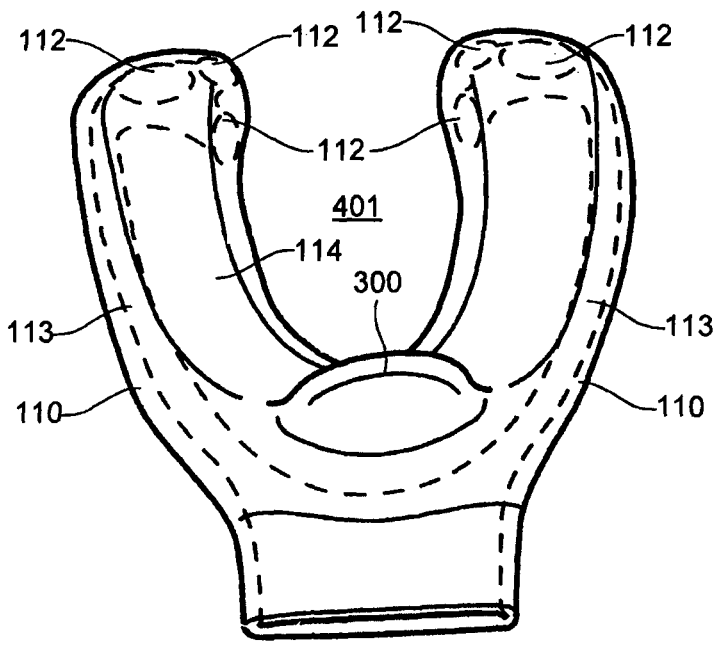
FIG. 4B is a schematic underside view of the breathing assist apparatus of FIG. 4A.
Figure 4C:
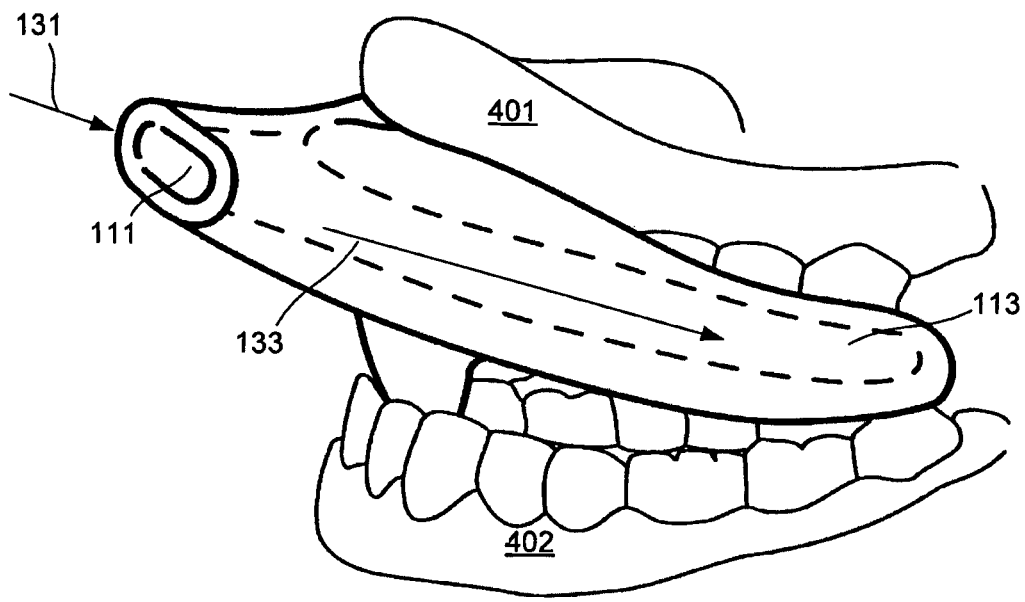
FIG. 4C is a schematic right side perspective views of the breathing assist apparatus of FIG. 4A.
Figure 4D:
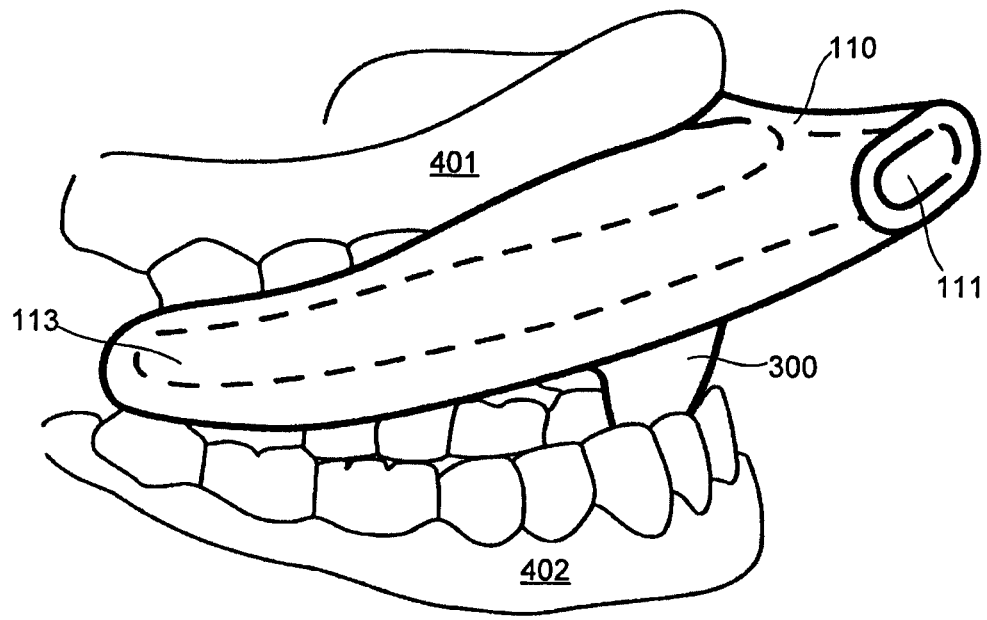
FIG. 4D is a schematic left side perspective views of the breathing assist apparatus of FIG. 4A.
Figure 4E:
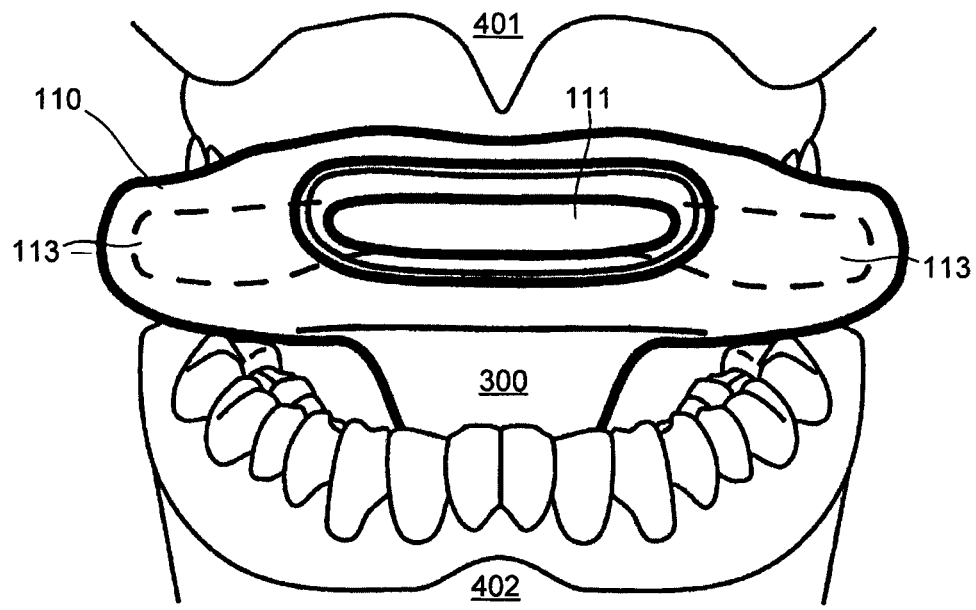
FIG. 4E is a schematic front view of the breathing assist apparatus of FIG. 4A.
Figure 4F:
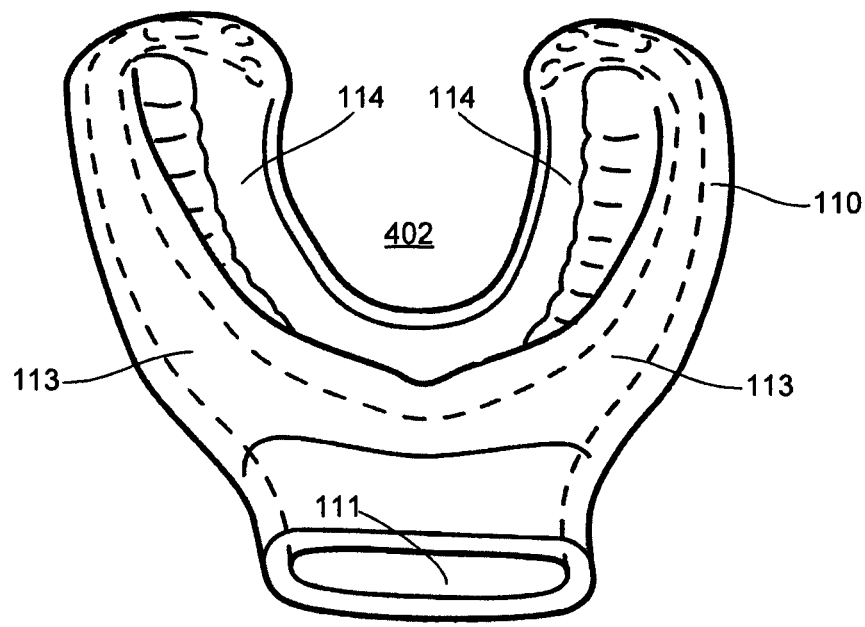
FIG. 4F is a schematic upper perspective view of the breathing assist apparatus of FIG. 4A.
Figure 4G:
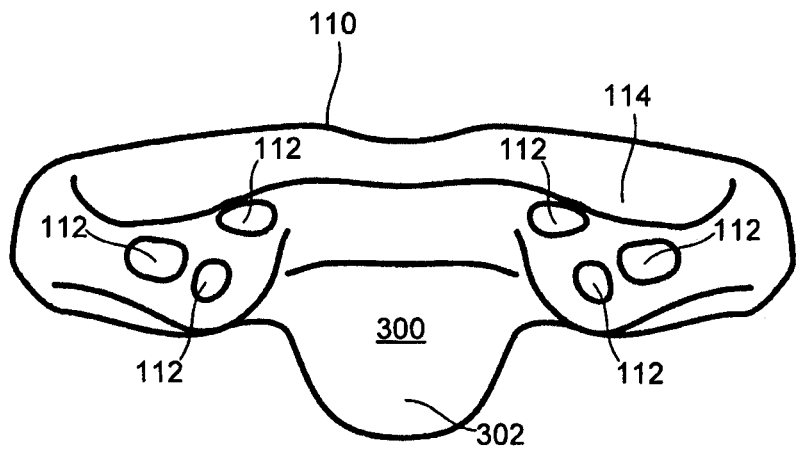
FIG. 4G is a schematic rear view of the breathing assist apparatus of FIG. 4A.
Figure 4H:
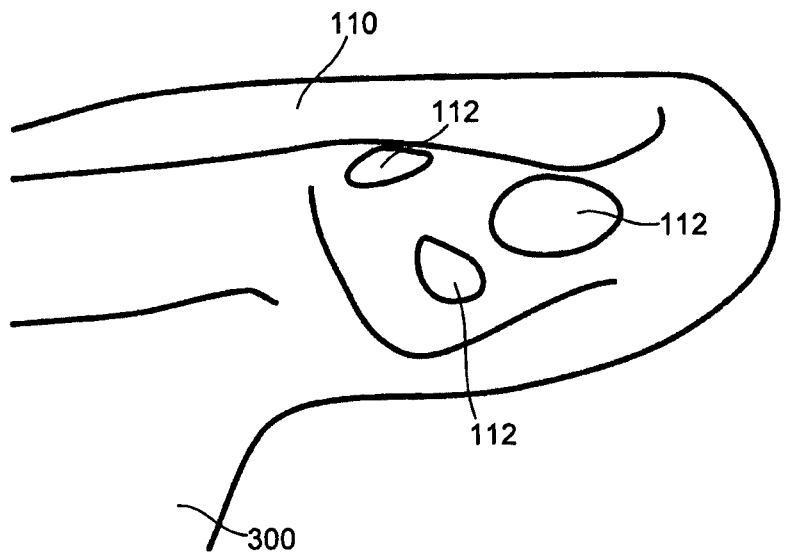
FIG. 4H is a schematic close up of part of FIG. 4G.
Figure 4I:
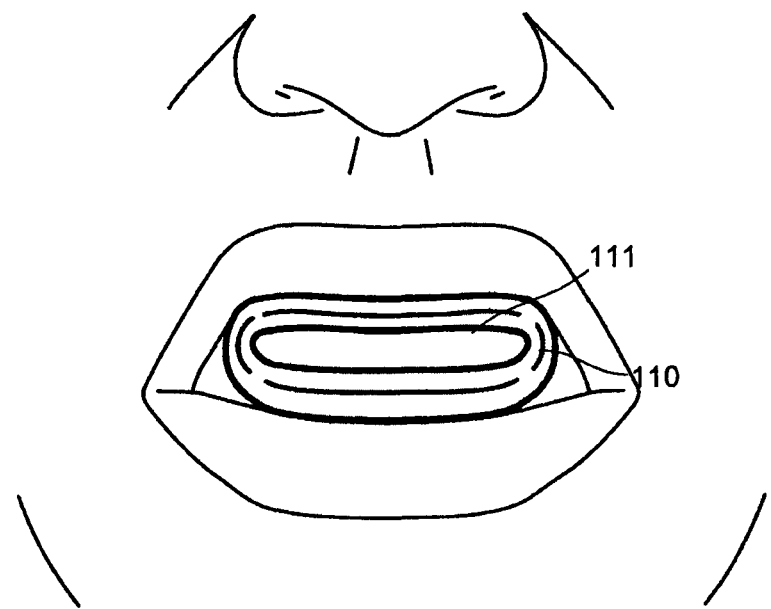
FIG. 4I is a schematic front view of the breathing assist apparatus of FIG. 4A in use.
Figure 4J:
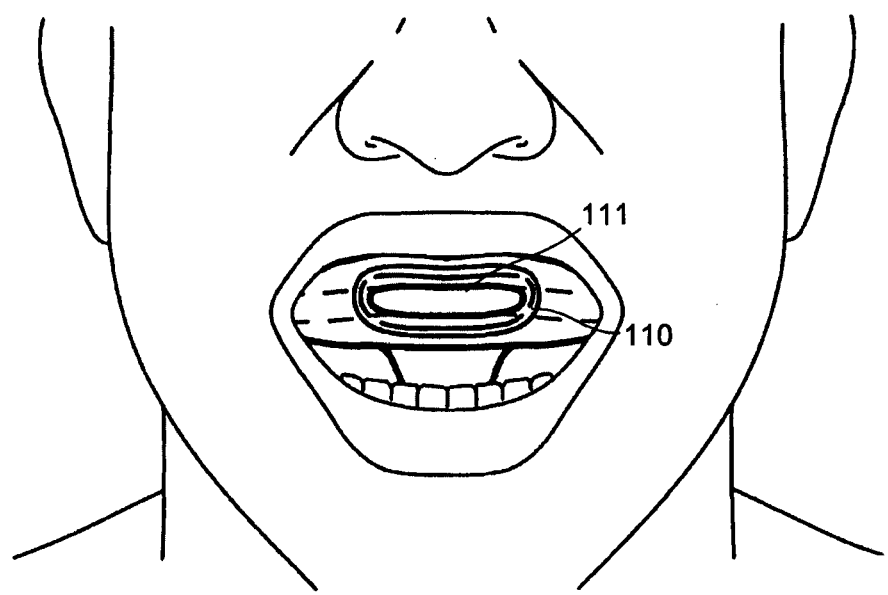
FIG. 4J is second a schematic front view of the breathing assist apparatus of FIG. 4A in use.
Figure 4K:
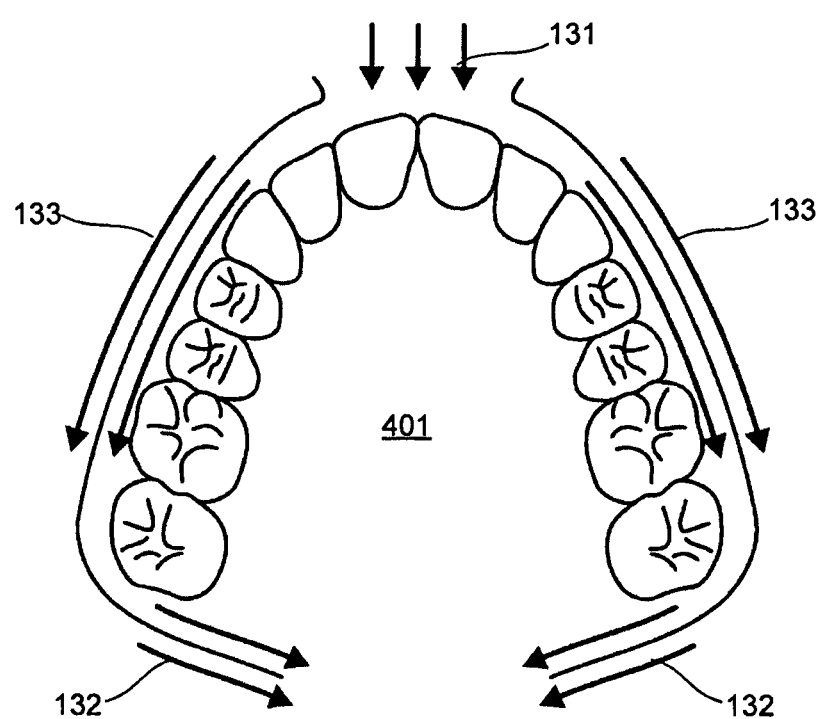
FIG. 4K is a schematic diagram showing air flow for the apparatus of FIGS. 4A to 4J.

In this example, a plurality of second openings are provided, as highlighted in FIGS. 4A, 4B and 4G, thereby maximising airflow into the posterior portion of the user's mouth.

It will be appreciated from the example of FIGS. 4A to 4J that the body can have a range of different shapes, and this will depend largely on the shape and size of the user's oral cavity. In this regard, the apparatus 100 is typically manufactured by having a dental professional obtain bite impressions of the user's maxillary and mandibular teeth. The bite impressions are used to create moulds, which are in turn used in shaping the body 110, providing the bite recess 114 and allowing positioning of the lingual flange 115.

The body 110 is typically formed from a heat and/or chemical cured acrylic resin or the like. However, soft acrylic or light cured composites, may be used to make the apparatus more quickly and cheaply, but these tend to not be as durable, and may therefore be more common for short-term use.

In any event, the body 110 is created including the channel 113 and first and second openings 111, 112, the outer surface of body 110 then being moulded using the moulds, thereby allowing the device to be custom made for each user. This ensures that the recess 114 correctly accommodates the user's maxillary teeth, thereby ensuring the apparatus is correctly positioned within the user's mouth. Similarly, the lingual flange 300 is positioned in accordance with the impressions of the user's bite, thereby ensuring that the upper and lower jaws are correctly aligned.

As a further alternative, the apparatus 100 can be made of a thermoplastic, such as Ethylene vinyl acetate (EVA), PolyShoK™, or the like. In this instance. the body 110 is formed as a blank including the airways in the form of the channels 113 and openings 111, 112. The user can then heat the body, for example, by boiling this in water. Once sufficiently heated, the user inserts the blank into their mouth, and clenches their teeth, thereby creating the recess 114, with the shape of this and the surrounding body 110 being moulded to the shape of the user's mouth, so that the apparatus 100 fits as intended. Such boil and bite arrangements for standard mouth guards and the like are well known in the art, and will not therefore be described in any further detail.

It will be appreciated from the above that further variations are also possible. For example, whilst the above described device includes a recess 114 for the maxillary teeth, the apparatus can additionally and/or alternatively, include a recess on an underside of the apparatus for receiving the mandibular teeth. However this is not essential and the use of the lingual flange provides efficient jaw alignment whilst obtaining a high degree of wearer comfort.

In one particular example, the recess 114 can be designed to engage the maxillary teeth so that the body is retained in position when a user opens their mouth. This provides enhanced comfort, whilst ensuring that the apparatus remains in an operative position even if the user opens their mouth during sleep. This is shown for example in FIGS. 4I and 4J, in which the body 110 remains in place when the user's jaws are partially opened.

Figure 5A:
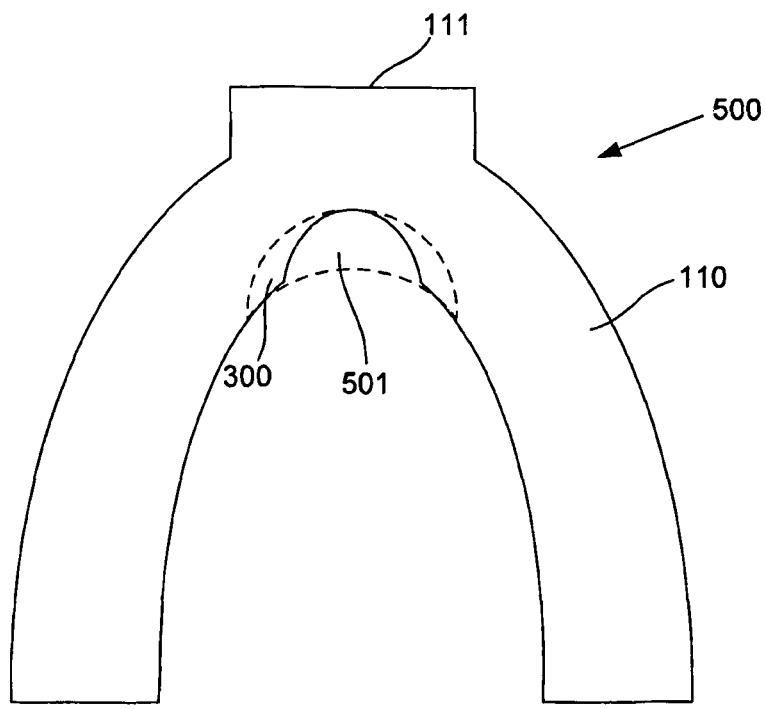
FIG. 5A is a schematic underside view of a fourth example of a breathing assist apparatus.
Figure 5B:
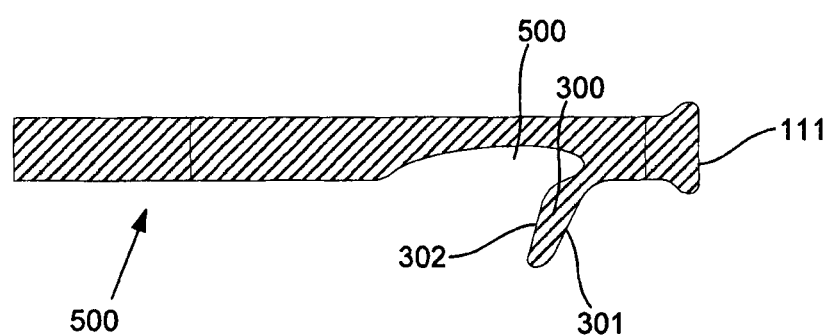
FIG. 5B is a schematic cross sectional side view of the apparatus FIG. 5A.

A fourth example of a breathing assist apparatus will now be described with reference to FIGS. 5A and 5B.

In this example, the apparatus 500 is substantially similar to that described above with respect to FIGS. 3A to 3C, and accordingly similar features will not be described in any detail.

In this example, the body 110 includes a tongue recess 501 provided in the second underside of the body 110, the tongue recess being positioned rearwardly of the lingual flange 300. In use, the user's tongue can be positioned within the tongue recess 501 in use, with a suction action acting to retain the user's tongue forwardly within the oral cavity. This in turn helps prevent, or at least further reduce, blockage of the user's airway by the tongue, thereby further assisting with breathing. In this example, the opening 111 may also be widened to accommodate the tongue recess within the body 110, without restricting airflow along the channels 113.

Figure 6A:
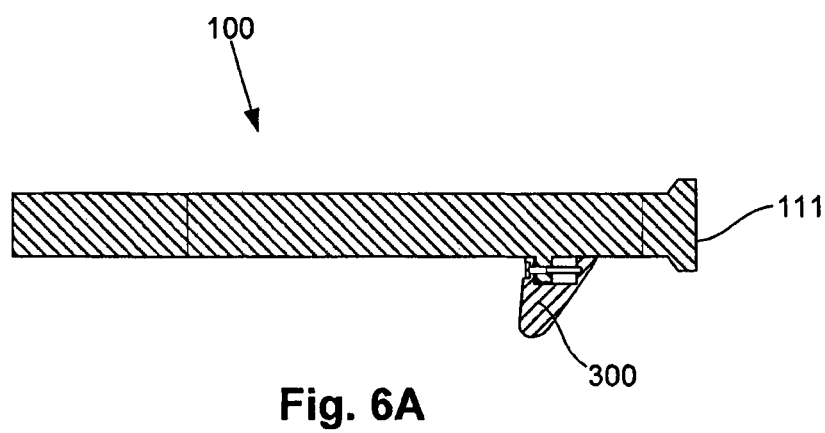
FIG. 6A is a schematic cross sectional side view of a fifth example of a breathing assist apparatus with a lingual flange in an advanced position; and, FIG. 6B is a schematic cross sectional side view of the apparatus FIG. 6A with the lingual flange in a retracted position.
Figure 6B:
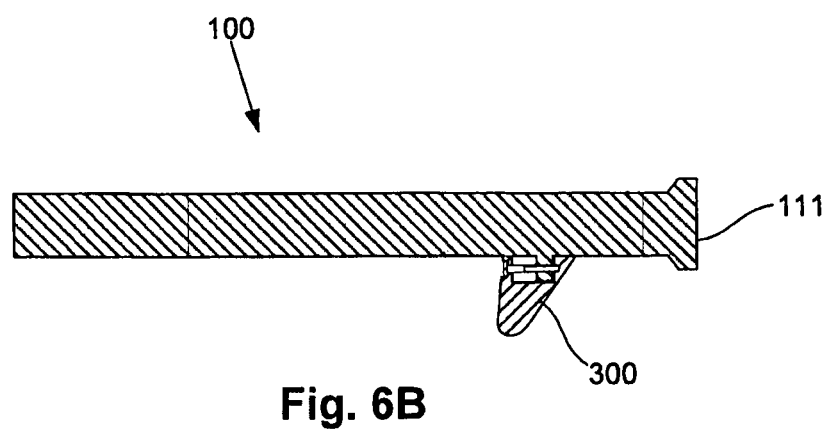

A fifth example of a breathing assist apparatus will now be described with reference to FIGS. 6A and 6B.

In this example, the apparatus 600 is substantially similar to that described above with respect to FIGS. 3A to 3C, and accordingly similar features will not be described in any detail.

In this example, the lingual flange 300 is movably mounted to the body 110. Whilst this can be achieved in any suitable manner, in one example, the lingual flange 300 includes a flange recess 601 for receiving a flange mounting 602 projecting from a lower surface of the body 110. A screw 603 is provided extending through the lingual flange 300 and the flange mounting 602, so that as the screw is rotated the relative position of the flange mounting 602 within the flange recess 601 is adjusted, thereby progressively moving the flange between an advanced position shown in FIG. 6A and a retracted position shown in FIG. 6B. It will therefore be appreciated that movably mounting the flange 300 to the body 110, allows the relative degree of mandibular advancement to be adjusted to thereby provide an optimum outcome for the user.

In any event, the above described apparatus provides a dental insert that provides an airway running from between the lips into the buccal sulcus and/or between the teeth then into the area over or behind the wisdom teeth, through the hamular notch and then opening into a region near or just off the soft palate. This provides an alternative airway, helping mitigate the impact of partial or total obstructions either in the nasal passages, soft palate or created by the tongue, thereby reducing the impact of such obstructions, and hence preventing snoring and OSA.

The provision of a lingual flange can be used to move a user's mandible forward, helping to prevent obstruction by the tongue, thereby maintaining a clear glossopharyngeal airway, with the degree of advancement being controlled depending on severity of symptoms. For example, this can be to the extremity of the neuromuscular zone of tolerance or beyond if necessary to clear tongue obstruction. The concave inner surface of the tongue flange, together with an optional tongue recess, can also act as a suction cup to hold the tongue forward.

In addition to this, maintaining alignment of the upper and lower jaws can reduce the impact of TMD.

The apparatus may also include a screw inserted into the lingual flange allowing the apparatus to be titratable for use with PSG (Polysomnograph) and EMG (Electromyograph).

It will be appreciated from the above described examples, that the use of an airway running from between the lips into the buccal sulcus and/or between the teeth then into the area over or behind the wisdom teeth, through the hamular notch and then opening into a region near or just off the soft palate could be implemented as part of existing insert that includes a body insertable into the oral cavity. Accordingly, the above described examples are for the purpose of illustration only and are not intended to be limiting.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that the airway can also be incorporated into other forms of device, such as existing mandibular advancement devices, including appliances for elastic advancement, advancement with connectors, tongue retaining devices, bimaxillary fixed appliances, bimaxillary occusal appliances, or the like. The above described arrangement is therefore for the purposes of example and is not intended to be limiting.

The claims defining the invention are as follows:

1. An apparatus for providing breathing assistance, the apparatus including:
    a) a body configured to be positioned within an oral cavity of the user and including a recess configured to receive the user's maxillary teeth;
    b) a first opening configured to extend beyond lips of a user to allow air from outside the oral cavity to be drawn in through the first opening;
    c) a second opening configured to be provided in the oral cavity to allow air to be directed into a posterior region of the oral cavity, wherein the second opening is configured to be provided behind teeth of the user; and,
    d) a channel connecting the first and second openings, the channel being configured to extend along at least part of a buccal sulcus of the user, wherein the channel is enclosed and the channel is configured to extend behind the teeth of the user to thereby allow air to flow through the channel directly into the posterior region of the oral cavity through an area behind the teeth of the user, and wherein the body includes the channel and at least part of the channel is configured to extend between the user's maxillary and mandibular teeth.

2. An apparatus according to claim 1, wherein at least part of the channel is configured to extend between the user's buccal mucosa and teeth.

3. An apparatus according to claim 1, wherein the channel is substantially U-shaped.

4. An apparatus according to claim 1, wherein the apparatus includes at least two second openings.

5. An apparatus according to claim 1, wherein the channel is configured to-extend through a hamular notch of the user.

6. An apparatus according to claim 1, wherein the second opening is configured to be provided on a lingual side of the teeth.

7. An apparatus according to claim 1, wherein the channel is configured to direct air into a region between the hard and soft palates of the user.

8. An apparatus according to claim 1, wherein at least a recess configured for receiving teeth of a user is molded for the user.

9. An apparatus according to claim 1, wherein the body includes a lingual flange configured to engage mandibular teeth to thereby maintain mandibular position.

10. An apparatus according to claim 9, wherein the lingual flange is mounted on a second side of the body, the recess being provided on a first opposing side of the body.

11. An apparatus according to claim 9, wherein the lingual flange is movably mounted to the body to thereby allow adjustment of a user's mandibular position.

12. An apparatus according to claim 9, wherein the lingual flange is configured to define a recess for receiving a user's tongue.

13. An apparatus according to claim 1, wherein the body includes a tongue recess configured to receive a user's tongue.

14. An apparatus according to claim 13, wherein the tongue recess is provided in a second side of the body, the recess being provided in an opposing first side of the body.

15. An apparatus according to claim 1, wherein a recess is configured to engage teeth of an upper jaw of the user, thereby retaining the body in position when a user opens their mouth.

16. An apparatus according claim 1, wherein the body is made of heat-cured acrylic resin.

* * * * *